United States Patent [19]
Cormier et al.

[11] Patent Number: 5,995,869
[45] Date of Patent: Nov. 30, 1999

[54] REDUCTION OF SKIN SENSITIZATION IN ELECTROTRANSPORT DRUG DELIVERY

[75] Inventors: Michel J. N. Cormier, Mountain View; James A. Matriano, Sunnyvale; Ronald P. Haak, Palo Alto; Peter E. Daddona, Menlo Park, all of Calif.

[73] Assignee: Alza Corporation, Palo Alto, Calif.

[21] Appl. No.: 08/872,723

[22] Filed: Jun. 11, 1997

Related U.S. Application Data

[60] Provisional application No. 60/019,617, Jun. 12, 1996.

[51] Int. Cl.$^6$ .................................................. A61N 1/30
[52] U.S. Cl. ............................................. 604/20; 607/152
[58] Field of Search ............................. 604/20; 607/115, 607/145, 152, 153

[56] References Cited

U.S. PATENT DOCUMENTS

| | | | |
|---|---|---|---|
| 4,885,154 | 12/1989 | Cormier | 424/10 |
| 4,942,883 | 7/1990 | Newman | 128/798 |
| 5,000,956 | 3/1991 | Amkraut et al. | 424/434 |
| 5,049,387 | 9/1991 | Amkraut | 424/435 |
| 5,077,054 | 12/1991 | Amkraut et al. | 424/486 |
| 5,118,509 | 6/1992 | Amkraut | 424/449 |
| 5,120,545 | 6/1992 | Ledger et al. | 424/449 |
| 5,130,139 | 7/1992 | Cormier et al. | 424/450 |
| 5,149,539 | 9/1992 | Ledger et al. | 424/449 |
| 5,160,741 | 11/1992 | Cormier | 424/450 |
| 5,171,576 | 12/1992 | Amkraut et al. | 424/449 |
| 5,202,130 | 4/1993 | Grant et al. | 424/617 |
| 5,304,379 | 4/1994 | Cormier et al. | 424/449 |
| 5,451,407 | 9/1995 | Cormier et al. | 424/448 |

FOREIGN PATENT DOCUMENTS

| | | |
|---|---|---|
| 0 318 776 | 6/1989 | European Pat. Off. . |
| 0467116 | 6/1991 | European Pat. Off. ..... A61K 31/415 |
| 0612525 | 8/1994 | European Pat. Off. ....... A61K 31/47 |
| WO 95/06497 | 3/1995 | WIPO . |
| WO 95/26782 | 10/1995 | WIPO . |

OTHER PUBLICATIONS

Rheins, et al., The Journal of Immunology, vol. 136, No. 3, pp. 867–876, Feb. 1, 1996, "Modulation of the Population Density of Identifiable Epidermal Langerhans Cells Assoicated with Enhancement or Suppression of Cutaneous Immune Reactivity."

Shimizu, et al., The Journal of Investigative Dermatology, vol. 101, No. 5, pp. 749–753 Nov. 1993, "Transepidermal Induction of Contact Hypersensitivity in Mice with a Water–Soluble Hapten."

Wille, J., et al,. Proceed. Intern. Symp. Control. Rel. Bioact. Mater., 22, pp. 119–120, No. 234 (1995), Controlled Release Society, Inc.,.

Drug Delivery Systems, Chapter 4, p. 155; Source: Reproduced from Behl C R et al., Iontophoretic Drug Delivery, Journal of Pharmaceutical Sciences, 78 (5), 355–360, 1989.

(List continued on next page.)

*Primary Examiner*—Wynn Wood Coggins
*Assistant Examiner*—Sharon Finkel
*Attorney, Agent, or Firm*—Owen J. Bates; D. Byron Miller; Steven F. Stone

[57] ABSTRACT

A device and method are provided for reducing or preventing skin sensitization in electrotransport drug delivery. The method involves co-administration of a countersensitizing agent, comprising cis-urocanic acid or an analog thereof, with the drug delivered via electrotransport. Novel drug reservoirs and electrotransport drug delivery systems, formulated with a countersensitizing agent as described herein, are provided as well.

28 Claims, 1 Drawing Sheet

OTHER PUBLICATIONS

Reeve, Vivienne E., et al., Am. J Clin Nutr 1995; 61:571–576, "pyridoxine supplementation protects mice from suppression of contact hypersensitivity indeced by 2–acetyl–4–tetrahydroxybutylimidazole (THI), ultraviolet B radiation (280–320 nm), or cis–urocanic acid[1-3]".

Jaksic, et al., Photochemistry and Photobiology, vol. 61, No. 3, pp. 303–309, (1995), "Cis–Urocanic acid synergizes with histamine for increased $PGE_2$ production by human keratinocytes: link to indomethacin–inhibitable UVB–induced immunosuppression".

Reeve, et al., Photochemistry and Photobiology, vol. 60, No. 3 pp. 268–273, 1994, "Lack of Correlation Between Suppression of Contact Hypersensitivity by UV Radiation and Photoisomerization of Epidermal Urocanic Acid in the Hairless Mouse".

Gilmour, et al., The Journal of Investigative Dermatology, vol. 101, No. 1, Aug., 1993, pp. 169–174, "Effect of Phototherapy and Urocanic Acid Isomers on Natural Killer Cell Function".

Guymer, et al., Transplantation, vol. 55, pp. 36–43, No. 1, Jan. 1993; "Urocanic Acid as an Immunosuppressant in Allotransplantation in Mice".

Hart, et al., The Journal of Immunology, vol. 150, pp. 4514–4523, No. 10, May 15, 1993, "Cis–Urocanic Acid Stimulates Human Peripheral Blood Monocyte Prostaglandin $E_2$ Production and Suppresses Indirectly Tumor Necrosis Factor–α Levels".

Reeve, et al., "Hazards of Urocanic Acid as a Cosmetic Ingredient". Photodermatol Photoimmunol Photomed 1991: 8: pp. 176–180.

Gruner, et al., The Journal of Investigative Dermatology, vol. 98, No. 4, Apr. 1992, pp. 459–462, "Inhibition of Skin Allograft Rejection and Acute Graft– Versus–Host Disease by Cis–Urocanic Acid".

Kurimoto, et al., The Journal of investigative Dermatology, pp. 69S–70S, "Deleterious Effects of Cis–Urocanic Acid and UVB Radiation on Langerhans Cells and on Induction of Contact Hypersensitivity are Mediated by Tumor Necrosis Factor–Alpha".

Gilmour, et al., Photodermatology Photoimmunology & Photomedicine, 1992/1993; 9: pp. 255–261, "The Effect of Ultraviolet B irradtiation, cis–urocanic acid and tumour necrosis factor–α on delayed hypersensitivity to Herpes Simplex Virus".

Moodycliffe, et al., Immunology 1992 77 pp. 394–399, "The Effect of Ultraviolet B Irradiation and Urocanic Acid Isomer on Dendritic Cell Migration".

Gilmour, et al., Photodermatol Photoimmunol Photomed 1990; 7: pp. 243–248, "The Effect of Histamine Receptor Antagonists on Immunosuppression Induced by the Cis–Isomer of Urocanic Acid".

Norval, et al., Photochemistry and Photobiology, vol. 49, No. 5, pp. 633–639, 1989, "Urocanic Acid Analogues and the Suppression of the Delayed Type Hypersensitivity Response to Herpes Simplex Virus".

Norval, et al., Photochemistry and Photobiology, vol. 50, No. 2, pp. 267–275, 1989, "Urocanic Acid and Immunosuppression".

Ross, et al., Photodermatology 1988: 5: pp. 9–14, "Systemic Administration of Urocanic Acid Generates Suppression of the Delayed Type Hypersensitivity Response to Herpes Simplex Virus in a Murine Model of Infection".

Ross, et al., Viral Immunology, vol. 1, No. 3, pp. 191–198, 1987/1988, "Induction of Suppression of Delayed Type Hypersensitivity to Herpes Simplex virus by Epidermal Cells Exposed to UV–Irradiated Urocanic Acid In Vivo".

Shimizu, et al., Immunology 1994 82 pp. 140–148, "Evidence that Ultraviolet B Radiation Induces Tolerance and Impairs Induction of Contact Hypersensitivity by Different Mechanisms".

Boddé, et al., Critical Reviews in Therapeutic Drug Carrier Systems, vol. 6, Issue 1 (1989), pp. 87–115, "The Skin complaince of Transdermal Drug Delivery Systems".

Räsänen, et al., The Langerhans Cell. Ed., 1988, vol. 172, pp. 253–260, "Suppression of Human Epidermal Cell Secreted and Membrane Interleukin–1 Production by Cis–Urocanic Acid".

Mitra, et al., The Journal of Investigative Dermatology, Abstracts: No. 7, p. 490 Cis–Urocanic Acid and Histamine Augment TNF–α Medicated Induction of Keratinocyte ICAM–1–Expression and Supress IFN–γ Induction of HLA–DR.

Shimizu, et al., TThe Journal of Investigative Dermatology, Abstracts: No. 458, p. 565, "UBV, TNFα and cis–Urocanic Acid Induce Tolerance to Hapten Via a Common, Non–TNFα–Dependent Mechanism".

Laurema, et al., The Journal of Investigative Dermatology, Abstract No. 644, p. 596, "Topical Cis–Urocanic Acid Suppresses Local Lymph Node Activation During Induction of Contact Hypersensitivity".

Roberts, et al., Clinical Research, vol. 38, No. 2, Apr. 1990, Cis–Urocanic Acid Induced Immunosuppression is Associated With A Prostaglandin–dependent Mechanism.

Fabo, et al., Photochem. Photobiol. 51 (Suppl) 1990, Abstract MPM–D12, "Cis–Urocanic Acid formulation by Ultraviolet B Irradiation of Skin Initiates UV Suppression of CHS in Mice".

Finlay–Jones, et al., Joint Meeting of the American Assoc. of Immun. and the Clinical Immunology society, Denver, CO, J. of Immunology 150 (8 part 2) 1993, "Cis–Urocanic Acid Stimulates Peripheral Blood Monocyte $PGE_2$ Production and Suppresses Indirectly TNFα Levels".

REDUCTION OF SKIN SENSITIZATION IN ELECTROTRANSPORT DRUG DELIVERY

RELATED APPLICATIONS

This application claims priority to U.S. provisional application Ser. No. 00/019,617, filed Jun. 12, 1996.

TECHNICAL FIELD

This invention relates generally to electrotransport drug delivery. More particularly, the invention relates to a method for preventing or reducing skin sensitization occurring with certain drugs or other components contained within electrotransport drug delivery systems. The invention further relates to drug reservoirs and drug delivery systems formulated so as to eliminate or reduce contact sensitization.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

However, many drugs are not suitable for passive transdermal drug delivery because of their size, ionic charge characteristics and hydrophilicity. One method of overcoming this limitation in order to achieve transdermal administration of such drugs is the use of electrical current to actively transport drugs into the body through intact skin. The method of the invention relates to such an administration technique, i.e., to "electrotransport" or "iontophoretic" drug delivery.

Herein the terms "electrotransport", "iontophoresis", and "iontophoretic" are used to refer to the transdermal delivery of pharmaceutically active agents by means of an applied electromotive force to an agent-containing reservoir. The agent may be delivered by electromigration, electroporation, electroosmosis or any combination thereof. Electroosmosis has also been referred to as electrohydrokinesis, electro-convection, and electrically induced osmosis. In general, electroosmosis of a species into a tissue results from the migration of solvent in which the species is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation". Any electrically assisted transport of species enhanced by modifications or alterations to the body surface (e.g., formation of pores in the skin) are also included in the term "alectrotransport" as used herein. Thus, as used herein, the terms "electrotransport", "iontophoresis" and "iontophoretic" refer to (1) the delivery ot charged drugs or agents by electromigration, (2) the delivery of uncharged drugs or agents by the process of electroosmosis, (3) the delivery of charged or uncharged drugs by electroporation, (4) the delivery of charged drugs or agents by the combined processes of electromigration and electroosmosis, and/or (5) the delivery of a mixture of charged and uncharged drugs or ageints by the combined processes of electromigration and electroosmosis.

In present electrotransport devices, at least two electrodes are used. Both of these electrodes are disposed so as to be in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the ionic substance to be driven into the body is positively charged, then the positive electrode (the anode) will be the active electrode and the negative electrode (the cathode) will serve as the counter electrode, completing the circuit. If the ionic substance to be delivered is negatively charged, then the cathodic electrode will be the active electrode and the anodic electrode will be the counter electrode.

Existing electrotransport devices additionally require a reservoir or source of the pharmaceutically active agent which is to be delivered or introduced into the body. Such drug reservoirs are connected to the anode or the cathode of the electrotransport device to provide a fixed or renewable source of one or more desired species or agents.

Thus, an electrotransport device or system, with its donor and counter electrodes, may be thought of as an electrochemical cell having two electrodes, each electrode having an associated half cell reaction, between which electrical current flows. Electrical current flowing through the conductive (e.g., metal) portions of the circuit is carried by electrons (electronic conduction), while current flowing through the liquid-containing portions of the device (i.e., the drug reservoir in the donor electrode, the electrolyte reservoir in the counter electrode, and the patient's body) is carried by ions (ionic conduction). Current is transferred from the metal portions to the liquid phase by means of oxidation and reduction charge transfer reactions which typically occur at the interface between the metal portion (e.g., a metal electrode) and the liquid phase (e.g., the drug solution). A detailed description of the electrochemical oxidation and reduction charge transfer reactions of the type involved in electrically assisted drug transport can be found in electrochemistry texts such as J. S. Newman, *Electrochemical Systems* (Prentice Hall, 1973) and A. J. Bard and L. R. Faulkner, *Electrochemical Methods, Fundamentals and Applications* (John Wiley & Sons, 1980).

The present invention is directed to a method for using such electrotransport drug delivery system so that sensitization of the skin or mucosal tissue is reduced or eliminated during drug administration. Sensitization is a two-phase process involving biological mechanisms totally distinct from those observed in skin irritation. The first phase in sensitization reactions is the induction phase where the skin is initially exposed to a sensitizing agent, such as a drug or other antigen. During this phase, generally no skin reaction occurs. In the induction phase, the sensitizing drug or antigen is presented to T-lymphocytes by the Langerhans cells of the epidermis, either in situ or in the draining lymph node. As a consequence, cells which recognize the antigen, proliferate and differentiate.

The second, subsequent phase, following the establishment of contact allergy, is elicitation where a subsequent re-exposure (i.e., contact with the skin) to the sensitizing drug or antigen results in a manifested skin reaction. This condition is known as allergic contact dermatitis. During elicitation, the antigen is once again presented mainly on Langerhans cells. The T-cells which have differentiated or clonally expanded upon prior exposure now migrate to the treated site and initiate a cascade of skin reaction events which result in local inflammation.

Contact sensitization is a completely different process than irritation. Irritation is caused by and therefore relieved by a different mechanism than that of sensitization. Irritation depends upon a variety of factors including, but not limited to, change in pH and bacterial overgrowth. Ultimaitely, irritation is the result of damage to the cells by cellular response to a toxic agent, i.e., one that irritates. Sensitization, on the other hand, is the result of an allergic cellular response to an agent which is not necessarily intrinsically toxic.

Immune tolerance is a different phenomenon from both sensitization and irritation. Immune tolerance is the state of prolonged unresponsiveness to a specific antigen. Tolerance to contact sensitization has been induced in adult animals by pretreatment of the skin site to which the sensitizing drug or antigen is applied with compounds that act to suppress the animal's immune system (see Rheins et al. (1986) *J. Immunol.* 136:867–876). Immune tolerance to contact sensitizers was induced in mice by application of arachidonic acid to the local site for several days prior to antigen application (Rheins et al., supra).

A number of countersensitizing agents have been proposed for reducing sensitization and/or irritation reactions associated with transdermal drug delivery. Countersensitizing and/or counter irritating agents which have been used in transdermal drug delivery include metabolic modulators which inhibit drug metabolism by skin enzymes (see U.S. Pat. Nos. 4,885,154 and 5,304,379 to Cormier et al.), corticosteroids such as hydrocoitisone (see U.S. Pat. Nos. 5,049,387 and 5,118,509 to Amkraut and U.S. Pat. Nos. 5,000,956, 5,077,054 and 5,171,576 to Amkraut et al.), antigen processing inhibiting agents such as ammonium chloride (see U.S. Pat. Nos. 5,120,545 and 5,149,539 to Ledger et al.), lysosomal uptake inhibiting agents such as monensin (see U.S. Pat. Nos. 5,130,139 and 5,160,741 to Cormier et al.) and calcium channel blocking agents such as verapamil (see U.S. Pat. No. 5,202,130 to Grant et al.). In addition, the use of corticosteroids such as hydrocortisone (see Int'l Pub. No. WO 95/26782, inventors Cormier et al.) and the buffering of reservoir pH at select ranges (see Int'l Pub. No. WO 95/06497, inventors Cormier et al.) have been proposed to lessen or eliminate skin irritation and/or sensitization associated with electrically assisted transdermal drug delivery.

Cis-urocanic acid has been proposed to be useful for inhibiting or preventing sensitizing effects encountered with passive transdermal delivery of certain drugs. See, e.g., European Patent Publication No. (312,525, published Aug. 31, 1994, and Wille et al., "Topical Delivery of Mast Cell Degranulating Agents for Treatment of Transdermal Drug-Induced Hypersensitivity," *Proceed. Intern. Symp. Control. Rel. Bioact. Mater.*, 22:119–120 (1995). In addition, it has been reported by Shimizu et al. in *J. Inv. Dermatol.*, pp. 749–753 (1993), that cis-urocanic acid could induce skin tolerance to a sensitizing drug.

The use of cis-urocanic acid or an analog thereof in reducing or preventing sensitization occurring in conjunction with electrotransport drug delivery is, however, novel and completely unsuggested by the art. An important advantage of using cis-urocanic acid or a cis-urocanic acid analog as a countersensitizing agent is that such compounds are naturally occurring compounds found in skin and body tissue (or metabolites of naturally occurring compounds) and thus use in conjunction with electrotransport drug delivery does not represent the introduction of foreign mater al. Another important advantage is the effectiveness of cis-urocanic acid or an analog thereof in reducing or preventing skin sensitization during electrotransport drug delivery.

DISCLOSURE OF THE INVENTION

Accordingly, it is a primary aspect of the invention to provide a method for reducing or preventing sensitization occurring in conjunction with electrotransport delivery of a drug.

It is another aspect of the invention to provide such a method which involves co-administering a countersensitizing agent along with the drug to be administered, wherein the countersensitizing agent is selected from the group consisting of cis-urocanic acid and analogs thereof.

It is still another aspect of the invention to provide a drug reservoir for use in an electrotransport drug delivery system, containing a pharmaceutical formulation comprising the drug to be administered and a countersensitizing agent as will be described in detail elsewhere herein.

It is a further aspect of the invention to provide an electrotransport drug delivery system having a drug reservoir containing a pharmaceutical formulation comprising the drug to be administered and a countersensitizing agent as described herein.

Additional aspects, advantages and novel features of the invention will be set forth in part in the description which follows, and in part will become apparent to those skilled in the art upon examination of the following, or may be learned by practice of the invention.

The present invention relates to the co-administration of a countersensitizing agent with a drug being delivered via electrotransport. The countersensitizing agent, as will be explained in detail elsewhere herein, is preferably cis-urocanic acid or an analog thereof.

It has now been found that cis-urocanic acid, along with certain analogs thereof, is useful in reducing or preventing sensitization of the skin or mucosa during electrotransport drug delivery. This is somewhat surprising, in view of the fact that the drugs and reservoir components involved in electrotransport delivery are quite different from those typically used in conjunction with passive transdermal delivery; further, the pathways by which components permeate through the skin in electrotransport arid passive transdermal delivery are entirely different. Additionally, a number of factors are important in iontophoretic skin permeation that are irrelevant in passive transdermal delivery, e.g., skin impedance, ionic strength of the drug formulation, state of ionization, current density used, and the like; similarly, a number of factors that are important in passive transdermal delivery are not important in electrotransport delivery. See, e.g., *Scrips' Drug Delivery Systems Report*, New York: PharmaBooks, Ltd., 1994, at page 155. It would not be expected, then, that a countersensitizing agent or any other drug formulation component which might be useful in passive transdermal delivery would by analogy be useful in electrotransport drug delivery.

A key advantage of using cis-urocanic acid, or analogs thereof, is that such compounds occur naturally in the skin (i.e., trans-urocanic acid is present in the skin, which is converted to the cis form upon exposure to ultraviolet radiation) and thus do not represent "foreign" materials as such. This is in contrast to prior methods for reducing sensitization such as co-delivery of a vasodilating agent (e.g., methyl nicotinate; see U.S. Pat. No. 5,451,407 to Cormier et al.), an anti-inflammatory agent, an antigen processing inhibitor, an agent capable of forming a complex with the drug administered, or, alternatively, delivering a nonsensitizing prodrug which releases the inactive conjugating moiety after administration.

In one embodiment of the invention, then, a method is provided for reducing or preventing sensitization of the skin or mucosa encountered during electrotransport drug delivery. The method involves co-administering a countersensitizing agent with the drug delivered via electrotransport. The drug and countersensitizing agent are administered co-extensively to a selected site on the human skin or mucosa from an electrotransport drug delivery device placed in drug and agent transmitting relationship to the skin or mucosa. The drug is typically although not necessarily one that is susceptible to inducing sensitization when administered at a therapeutically effective rate. That is, as sensitization may be encountered as a result of other components present in the pharmaceutical formulation being delivered, e.g., enhancers or the like, the countersensitizing agent will act to reduce or prevent such sensitization as well, regardless of whether or riot the drug administered is one that tends to cause sensitization.

In another embodiment, a drug reservoir is provided for incorporation into an electrotransport drug delivery system, the reservoir containing a pharmaceutical formulation as described above, i.e., a drug to be delivered and a countersensitizing compound. The drug reservoir is formed from components typically used to prepare reservoirs for electrotransport delivery; such materials will be known to those skilled in the art or may, be readily deduced from a review of the relevant literature.

In a further embodiment, an electrotransport drug delivery system is provided which incorporates the aforementioned hydrogel reservoir. The system contains a donor electrode, a counter electrode, a source of electrical power, and the reservoir containing the drug to be delivered and the countersensitizing agent, typically present as part of the donor electrode.

MODES FOR CARRYING OUT THE INVENTION

Figure 1:
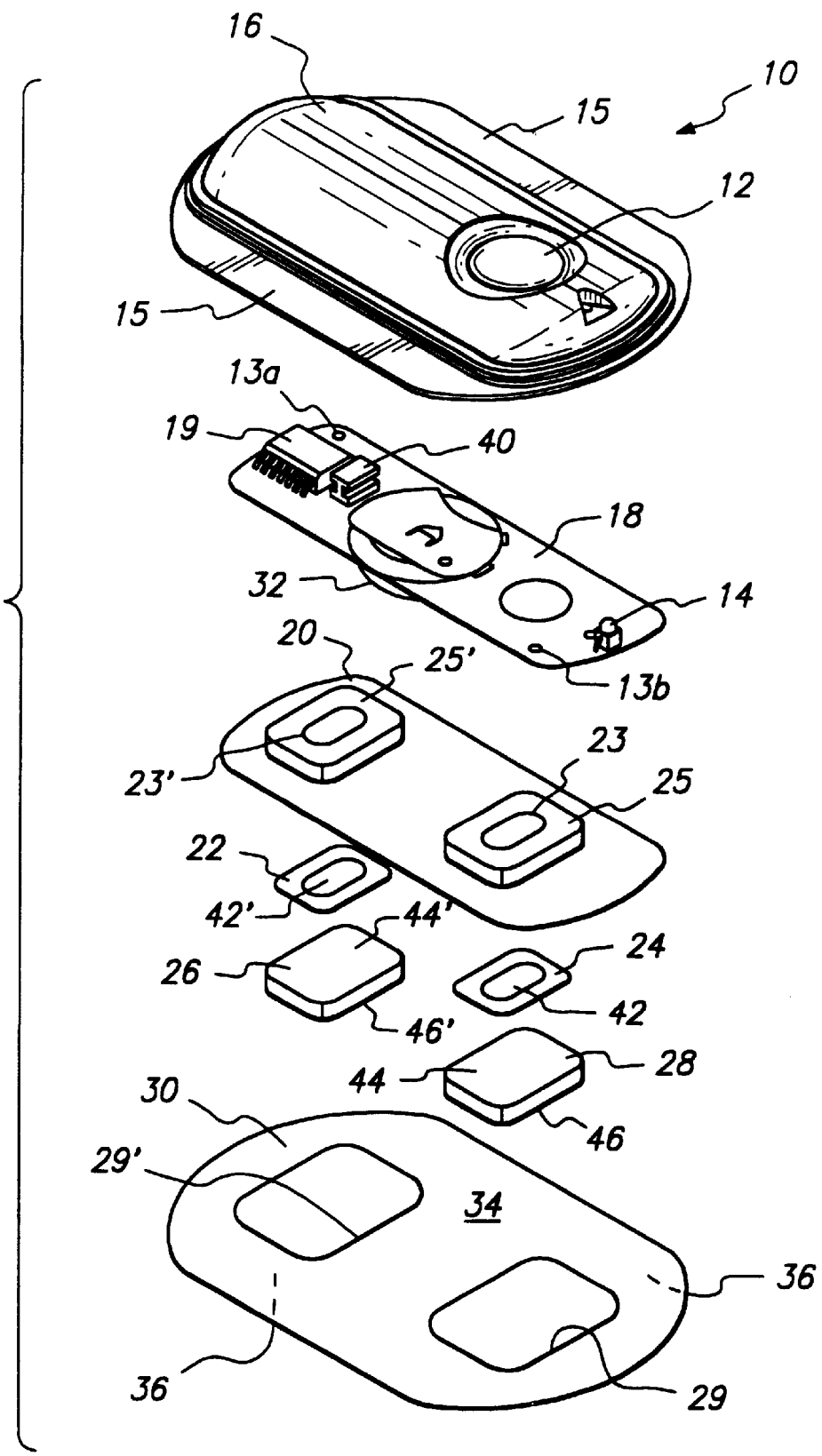
FIG. 1 is a perspective exploded view of one embodiment of an electrotransport drug delivery system which may be used within drug formulations and methods of the present invention.

Before describing the present invention in detail, it is to be understood that this invention is not limited to particular drugs, carriers, electrotransport delivery systems, or the like, as such may vary. It must be noted that, as used in this specification and the appended claims, the singular forms "a", "an" and "the" include plural referents unless the context clearly dictates otherwise. Thus, for example, reference to "a drug" includes a mixture of two or more drugs, reference to "a countersensitizing agent" includes two or more such agents, and the like. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and method, are described herein. In a first embodiment of the invention, a countersensitizing agent is co-administered with a drug being delivered via electrotransport The drug and countersensitizing agent are present in a single formulation in a drug reservoir contained within an electrotransport drug delivery system. The drug and agent are simultaneously delivered, i.e., administration is; "co-extensive." In this embodiment, co-extensive administration of the drug and the agent extends over the entire period of drug delivery.

In a second embodiment of the invention, the drug and the countersensitizing agent are administered co-extensively for a period of time sufficient to induce tolerance. Once tolerance has been induced through the co-extensive administration of the drug with the agent, the administration of the agent may be stopped and thereafter the drug administered without any agent and without danger of sensitizing the patient and causing adverse skin reactions. Once tolerance has been induced by co-extensively administering the drug and the countersensitizing agent, the drug may be thereafter administered following a regimen that is sufficient to maintain the induced tolerance in the individual patient. Generally, continuous readministration of the drug after the induction of tolerance will maintain that induced tolerance in the individual patient. However, in many instances continuous readministration of the drug is not necessary to maintain induced tolerance to the drug. Depending on a number of factors including the particular drug being administered and the individual patient, intermittent readministration of the drug after tolerization may be sufficient to maintain tolerance. Thus, once tolerance has been induced, the re-application of the drug without the countersensitizing agent for periods of on the order of several weeks out of a period extending over about six to twelve months is in many cases sufficient to maintain the induced tolerance in the individual patient.

The drug reservoir in which the formulation containing the drug and the countersensitizing agent is held may be comprised of any material that is useful in conjunction with electrotransport drug delivery; generally, polymeric hydrogel matrices are preferred. The relative quantities of drug and countersensitizing agent incorporated into the drug reservoir are such that: (1) the drug is present in an amount such that delivery will be at a therapeutically effective rate for the duration of a predetermined drug delivery period; and (2) the countersensitizing agent is present in an a-mount such that delivery of the countersensitizing agent will be effective to reduce or eliminate sensitization occurring as a result of the drug or some other component present in the reservoir, e.g., an enhancer or the like.

Most drugs (i.e., about 70%) that are administered using electrotransport drug delivery devices carry a positive charge and are thus delivered from an anodic reservoir. Delivery of these drugs is typically effected from formulations having a pH in the range of about 5 to about 7 because the skin is most permeable to cations in this pH range. However, the desired pH of the drug formulation additionally depends on other factors, such as the stability of the drug, the solubility of the drug, and the like.

For formulations in which the countersensitizing agent is cis-urocanic acid, which has an isoelectric point at about pH 5, the cis-urocanic acid will carry a net negative charge when the pH of the formulation is greater than about 5 and a net positive charge when the pH of the formulation is less than about 5. When the pH of the formulation is about 5, the cis-urocanic acid will be essentially neutral. Accordingly, a cationic drug and cis-urocanic acid as the countersensitizing agent can be co-extensively delivered by electromigration when placed in the anodic reservoir of an electrotransport device if the pH of the formulation is less than about 5. Similarly, an anionic drug and cis-urocanic acid can be co-extensively delivered by electromigration from the cathodic reservoir if the pH of the formulation is greater than about 5. Alternatively, if the pH of the formulation is about the same as the isoelectric point of the countersensitizing agent, e.g, about pH 5 if the countersensitizing agent is cis-urocanic acid, the countersensitizing agent can be co-extensively delivered by electroosmosis, with electromigration and/or electroosmotic delivery of the drug, from the anodic reservoir for cationic drugs or the cathodic reservoir for anionic drugs. On the other hand, for cationic drug formulations in which the predetermined pH is greater than the isoelectric point of the countersensitizing agent which would thus carry a net negative charge, the countersensitizing agent may be delivered by means of reversing (alternating) the polarity of the electrotransport-driving current either before, during or after, preferably before, electrotransport drug delivery using normal polarity.

The transdermal flux of the countersensitizing agent, whether by electromigration, electroosmosis or a combination thereof, is preferably at least about 1 $\mu g/cm^2/hr$, which is believed to be the minimum flux of cis-urocanic acid (and some analogs thereof) necessary to inhibit contact sensitization.

As used herein, the terms "drug," "therapeutic agent" or "pharmaceutically active agent" are intended to mean any chemical material or compound which induces some beneficial or therapeutic effect, and is capable of being delivered by electrotransport. Examples of such substances will be set forth below.

The countersensitizing agents used in conjunction with the present method are cis-urocanic acid and analogs thereof. Suitable analogs of cis-urocanic acid are generally, although not necessarily, selected from the group consisting of cis and trans isomers of 2-methylurocanic acid, cis and trans isomers of 1-furanacrylic acid, cis and trans isomers of 2-pyrrole acrylic acid, cis and trans isomers of 2-thiopheneacrylic acid, cis and trans isomers of 3-thiopheneacrylic acid, dihydrourocanic acid, imidazolepyruvic acid, imidazoleacetic acid, hydantoin 5-propionic acid, 2-pyridinea(,rylic acid, 3-pyridineacrylic acid, and imidazolonepropionic acid. Such compounds may be obtained commercially, or they may be synthesized using standard techniques of synthetic organic chemistry; see, e.g., European Patent Publication No. 612,525, cited previously, and references mentioned therein. With some of these analogs, it may be necessary to work with a formulation having a pH different than that identified above (i.e., 5 with respect to cis-urocanic acid and certain analogs), in order to optimize the flux of the selected countersensitizing agent. The choice of a suitable pll may be readily deduced by those skilled in the art of electrotransport drug delivery, using routine methodology.

According to the invention, the drug to be delivered and the countersensitizing agent are contained in a drug reservoir within an electrotransport delivery system. In addition, although it will be generally preferred to include a countersensitizing agent in the drug reservoir, it is also possible to incorporate a countersensitizing agent in the counter reservoir if other sensitizing components are present therein. The drug delivery system is then placed in drug and agent transmitting relationship to the selected body surface, as will be described in detail below.

As noted above, drugs, therapeutic or active agents usefull in connection with the present invention include any pharmaceutical compound or chemical that is capable of being delivered by electrotransport. Co-administration of a countersensitizing agent according to the invention with known sensitizing drugs will prevent or reduce sensitization. This invention has utility in connection with the delivery of sensitizing drugs within any of the broad class of drugs normally delivered through body surfaces and membranes, including skin. In general, this includes sensitizing agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as ranitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetrics, prostaglandins, psychostimulants, sedatives and tranquilizers. The invention is also useful in conjunction with reducing or preventing sensitization occurring as a result of electrotransport delivery of proteins, peptides and fragments thereof, whether naturally occurring, chemically synthesized or recombinantly produced. The invention may additionally be used in conjunction with the delivery of nucleotidic drugs, including oligonucleotide drugs, polynucleotide drugs, and genes.

With respect to the co-extensive delivery of countersencitizing agents with sensitizing peptides, polypeptides, proteins, nucleotidic drugs, and other such species, these substances typically have a molecular weight of at least about 300 daltons, and more typically have a molecular weight of at least about 300 to 40,000 daltons. Specific examples of peptides and proteins in this size range include, without limitation, LHRH, LHRH analogs such as goserelin, buserelin, gonadorelin, napharelin and leuprolide, GHRH, GHRF, insulin, insultropin, calcitonin, octreotide, endorphin, TRH, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, $\alpha$ANF, growth factors such as growth factor releasing factor (GFRF), $\beta$MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostnol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, resin inhibitors, thymosin alpha-1, thrombolytics, TNF, vaccines, vasopressin antagonists analogs, alpha-1 antitrypsin (recombinant), and TGF-beta.

It will be appreciated by those working in the field that the present method can be used in conjunction with a wide variety of electrotransport drug delivery systems, as the method is not limited in any way in this regard. For examples of electrotransport drug delivery systems, reference may be had to U.S. Pat. Nos. 5,147,296 to Theeuwes et al., 5,080,646 to Theeuwes et al., 5,169,382 to Theeuwes et al., and 5,169,383 to Gyory et al., the disclosures of which are incorporated by reference herein.

FIG. 1 illustrates a representative electrotransport delivery device that may be used in conjunction with the present invention. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19,40, electrodes 22,24, and hydrogel drug reservoirs 26,28, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, e.g., a "beeper". Drug is delivered through the patient's skin by electrotransport, e.g., on the arm, over the predetermined delivery interval.

Anodic electrode 22 is preferably comprised of silver and cathodic electrode 24 is preferably comprised of silver chloride. Both reservoirs 26 and 28 are preferably comprised of polymeric gel materials. Electrodes 22,24 and reservoirs 26,28 are retained by lower housing 20.

A liquid drug solution or suspension is contained in at least one of the eservoirs 26 and 28. Drug concentrations in the range of approximately $1 \times 10^{-4}$ M to 1.0 M or more can be used, with drug concentrations in the lower portion of the range being preferred. Typically, the reservoir containing the drug will also contain the selected countersensitizing agent, in an amount and concentration effective to provide the flux necessary to reduce or prevent sensitization of the skin or mucosa.

As noted earlier herein, other components may be present in the drug reservoir or in the counter reservoir which could cause sensitization. examples of such components include flux enhancers or other "excipients," e.g., fatty acids and 1-dodecylazacycloheptan-2-one (see, U.S. Pat. No. 5,023,085 to Francoeur et al.), ion exchange resins, e.g., cation exchange resins (poly (acrylic phosphoric acids) and poly (acrylic glycolic acids)) and anionic exchange resins (polyvinyl amines, poly epichlorohydrin/tetraethylenetriamines, polymers containing pendant amine groups) buffers, or the like. Other agents may be present in a polymeric hydrogen matrix reservoir that can be transported into the skin during electrotransport drug delivery and can induce a sensitization reaction. Examples of such "polymeric matrix components" include, for example, unreacted monomer species, partially reacted polymeric species, polymer decomposition products, chemical cross-linking agents, residual blowing agents, release agents, antioxidants, etc. Accordingly, including a countersensitizing agent in the drug reservoir or in the counter reservoir will be effective in reducing or preventing sensitization resulting from these components as well.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom ot movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lovier housing 20 and retains the electrodes and drug reservoirs within housing depression 25, 25' as well as retains lower housing 20 attached to upper housing 16.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

(a) Preparation of Cis-Urocanic Acid Solution:

Sodium hydroxide (50 ml, 1.0 N) was added to 6.905 gm of trans-urocanic acid ("TUA") (Sigma Chemical Co., St. Louis, Mo.). The solution (pH 8) was dispensed into three 10-cm diameter Petri dishes. The dishes containing the TUA solution were irradiated for six hours with a 200 watt Hanovia Analytic Quartz mercury vapor lamp equipped with a 250–360 nm filter. The distance of the TUA solution from the lamp was 30 cm. Following irradiation, the solutions were combined and adjusted to pH 4.5 by the addition of hydrochloric acid (10 ml, 5.0 N); distilled water was added to bring the solution to a final total volume of 100 ml. This treatment resulted in the formation of a suspension. The particulate matter in the suspension was separated from the supernatant by centrifugation (4000×g, 5 min). The pellet thus formed was extracted with 100 ml water and the extracts were combined and lyophilized. The lyophilized powder was extracted three times with ethanol (200 proof) and the extracts were combined, dried and lyophilized to yield 2 gm white powder containing cis-urocanic acid and trans-urocanic acid in a 70:20 ratio as determined by HPLC and proton NMR analysis. The lyophilized powder was resuspended in water, neutralized with sodium hydroxide, 1N, and purified to greater than 99% cis-ulocanic acid using ion exchange chromatography (Bio-Rad®) AG1-X8 resin, 100–200 mesh, acetate form) and elution with 100 mM acetic acid. This sample was used for the tests described below.

(b) Evaluation of Inhibition of Sensitization to Ketoprofen in Vivo in a Human Patient Population by Electrically Assisted Transdermal Co-administration of Cis-Urocanic Acid with Ketoprofen:

Ketoprofen is a known skin sensitizing drug in humans. In order to test the counter-sensitizing effect of cis-urocanic acid on the contact sensitizing effect of ketoprofen, conventional electrotransport drug delivery devices may be prepared using methods and materials known in the art.

Donor formulations are made containing 30 mM ketoprofen sodium salt and 30 mM cis-urocanic acid sodium salt. Control formulations are made containing 30 mM ketoprofen and/or saline. The formulations are gelled with 3 wt. % hydroxyethyl cellulose ("HEC". The pH of all formulations is approximately 8. At this pH, both ketoprofen and cis-urocanic acid have a net negative charge.

Normal individuals are randomly assigned to a test group (ketoprofen and cis-urocanic acid), a control group (ketoprofen and saline) and a placebo group (saline). The electrotransport drug delivery devices are set at a current density of 100 $\mu A/cm^2$, and are applied for 6 hours and thereafter removed. This procedure is nine times over a period of three weeks. Following the last application, the individuals are rested for one week and then all of the members of each group are challenged with the same device containing ketoprofen with saline.

Results indicate that cis-urocanic acid inhibits contact sensitization to ketoprofen.

EXAMPLE 2

Inhibition of Sensitization to Tetracaine in Hairless Guinea Pigs by Electrically Assisted Transdermal Co-Administration of Cis-Urocanic Acid with Tetracaine: Anodic Co-delivery of Neutrally Charged Cis-Urocanic Acid with a Cationic Drug Donor formulations are made containing 30 mM tetracaine hydrochloride and cis-urocanic acid at various concentrations from 10 mM to 200 mM. Control formulations are made containing only tetracaine or saline. The formulations are gelled with 3 wt. % HEC. The iso-elecric point of cis-urocanic acid is about pH 5. The pH of all formulations is about 5. At this pH, tetracaine is cationic while cis-urocanic acid is substantially neutral.

In vitro transdermal electrotransport fluxes are evaluated through heat-separated hairless guinea pig epidermis. The electrotransport flux studies are performed in triplicate for each experimental condition. Each cell is connected to a constant current source set at a current density of 30 $\mu A/cm^2$. Samples are collected from the receptor compartments and analyzed for drug concentration by high performance liquid chromatography. Tetracaine flux is about 10 $\mu g/cm^2$ h from all tetracaine-containing formulations. Cis-urocanic acid flux is concentration dependent and ranges between 1 and 5 $\mu g/cm^2$ h.

For induction of sensitization to tetracaine, hairless guinea pigs receive electrotransport systems containing an anode hydrogel with the formulations described above on one side of the animal. The electrotransport systems, which are set to deliver an electrotransport drive current having a current density of 30 $\mu A/cm^2$, are applied for 4 hours and thereafter removed. This is repeated three times every other day after the first exposure. Each of the formulations described above are tested using this protocol on a group of about ten guinea pigs. The animals are then rested for 1–2 weeks before challenge.

Approximately one to two weeks after the last induction with an electrotransport system, the guinea pigs are challenged with a 1 h application of tetracaine alone. Erythema and edema scores are taken 2, 24, 48, and 72 h after removal of the challenge electrotransport system. The erythema/edema scoring evaluation is done using a modification of the Draize method. Results indicate that cis-urocanic acid inhibits contact sensitization to tetracaine.

EXAMPLE 3

Inhibition of Sensitization to Tetracaine in Hairless Guinea Pigs by Transderma Electrotransport Co-Administration of Cis-Urocanic Acid with Tetracaine: Anodic Co-Delivery of Cationic Cis-Urocanic Acid with a Cationic Drug Donor formulations are made containing 30 mM tetracaine hydrochloride and cis-urocanic acid at various concentrations from 10 mM to 100 mM. Control formulations are made containing 30 mM tetracaine and/or saline. The formulations are gelled with 3 wt. % HEC. The pH of all formulations is adjusted to a level between 2 and 4 by addition of hydrochloric acid. At this pH range, both tetracaine and cis-Urocanic acid have a net positive charge.

In vitro transdermal electrotransport fluxes are evaluated as described in Example 2. A current density (anodic polarization) of 30 $\mu A/cm^2$ is used. Tetracaine flux ranges from about 3 to about 20 $\mu g/cm^2$ h. Ci-urocanic acid flux ranges from about 1 to about 20 $\mu g/cm^2$ h.

Induction and elicitation of sensitization to tetracaine is performed as described in Example 2. Results indicate that cis-urocanic acid inhibits contact sensitization to tetracaine.

EXAMPLE 4

Inhibition of Sensitization to Ketoprofein Hairless Guinea Pigs by Transdermal Electrotransport Co-Administration of Cis-Urocanic Acid with Ketoprofen: Cathodic Co-Delivery of Anionic Cis-Urocanic Acid with an Anionic Drug Donor formulations are made containing 30 mM ketoprofen sodium salt and 30 mM cis-urocanic acid sodium salt.

Control formulations are made containing 30 mM ketoprofen and 30 mM NaCl or saline. The formulations are gelled with 3 wt. % HEC. The pH of all formulations is about 8. At this pH, ketoprofen and cis-urocanic acid are each negatively charged.

In vitro transdermal electrotransport fluxes are evaluated as described in Example 2. A current density of 100 $\mu$A/cm$^2$ is used. Ketoprofen as well as cis-urocanic acid flux is about 20 $\mu$g/cm$^2$ h from all ketoprofen-containing formulations.

Induction and elicitation of sensitization to ketoprofen is performed as described in Example 2. The electrotransport systems are set at a current density of 100 $\mu$A/cm$^2$ and are applied for 6 hours and thereafter removed. This is repeated nine times every other day after the first exposure. Results indicate that cis-urocanic acid inhibits contact sensitization to ketoprofen.

EXAMPLE 5

Inhibition of Sensitization to Calcitonin-Gene-Related-Peptide ("CGRP") in Hairless Guinea Pigs by Transdermal Electrotransport Co-Administration of Cis-Urocanic Acid with CGRP: Alternating Polarity Co-Delivery of Anionic Cis-Urocanic Acid with a Cationic Drug Donor formulations are made containing 1 mM Calcitonin-Gene-Related-Peptide ("CGRP") and 30 mM cis-urocanic acid sodium salt. Control formulations are made containing 1 mM CGRP and 30 mM NaCl or saline. The formulations also contain a chlorides source and are gelled with 3 wt. % HEC. The pH of all formulations is about 7.5. At this pH, CGRP is positively charged while cis-urocanic acid is negatively charged.

In vitro transdermal electrotransport fluxes are evaluated as described in Example 2. A current density (anodic polarization) of 100 $\mu$A/cm$^2$ is used. Every 5 minutes the current is reversed (cathodic polarization) for about 1 minute duration, after which the polarity reverts back to anodic polarization. CGRP flux is about 1 $\mu$g/cm$^2$ h from all CGRP-containing formulations. Cis-urocanic acid flux is about 5 $\mu$g/cm$^2$ h.

Elicitation of sensitization to CGRP is performed as described in Example 2. The electrotransport systems are set at a current: density of 100 $\mu$A/cm$^2$ (anodic polarity to deliver only CGRP in the challenge) and are applied for 6 hours and thereafter removed. This is repeated nine times every other day after the first exposure. Results indicate that cis-urocanic acid inhibits contact sensitization to CGRP.

We claim:

1. A method for preventing or inhibiting sensitization of the skin or mucosa by a sensitizing agent during electrotransport delivery of a drug, comprising co-extensively administering to a selected site on the skin or mucosa, (a) the drug; and (b) a countersensitizing agent selected from the group consisting of cis-urocanic acid and analogs thereof, at a rate of at least about 1 $\mu$g/cm$^2$/hr, wherein the drug and the countersensitizing agent are in a formulation present in a drug reservoir contained in an electrotransport drug delivery device placed in drug and agent transmitting relationship to the skin or mucosa.

2. The method of claim 1, wherein the sensitizing agent is the drug, an excipient, an ion exchange resin, or a polymeric matrix component.

3. The method of claim 1, wherein the sensitizing agent is the drug.

4. The method of claim 3, wherein the drug and the countersensitizing agent are co-extensively administered over an entire redetermined delivery period.

5. The method of claim 3, wherein the drug and the countersensitizing agent are co-extensively administered for a period of time sufficient to induce tolerance to the drug.

6. The method of claim 3, wherein the drug is one that is susceptible ti inducing sensitization when administered via electrotransport at a therapeutically effective rate.

7. The method of claim 1, wherein the countersensitizing agent is cis-urocanic acid.

8. The method of claim 1, wherein the countersensitizing agent is an analog of cis-urocanic acid.

9. The method of claim 8, wherein the analog of cis-urocanic acid is selected from the group consisting of cis and trans isomers of 2-methylurocanic acid, cis and trans isomers of 1-furanacrylic acid, cis and trans isomers of 2-pyrrole acrylic acid, cis and trans isomers of 2-thiopheneacrylic acid, cis and trans isomers of 3-thiopheneacrylic acid, dihydrourocanic acid, imidazolepyruvic acid, imidazoleacetic acid, hydantoin 5-propionic acid, 2-pyridineacrylic acid, 3-pyridineacrylic acid, and imidazolonepropionic acid.

10. The method of claim 8, wherein the analog of cis-urocanic acid is 2-methylurocanic acid.

11. The method of claim 1, wherein the countersensitizing agent is administered at a rate effective to inhibit the induction of sensitization.

12. The method of claim 1, wherein the formulation has a pH at which both the drug and the countersensitizing agent are anionic.

13. The method of claim 1, wherein the formulation has a pH at which both the drug and the countersensitizing agent are cationic.

14. The method of claim 7, wherein the formulation has a pH at which the drug is cationic and at least a portion of the cis-urocanic acid has a neutral charge.

15. The method of claim 1, wherein the formulation has a pH at which one of the drug and the countersensitizing agent is cationic and the other is anionic and further wherein both are administered from the reservoir by an alternating polarity electrotransport current.

16. An electrotransport agent delivery device comprising a donor electrode, a counter electrode, and a source of electrical power adapted to be electrically connected to the donor and counter electrodes, a drug reservoir comprised of a polymeric carrier matrix and, incorporated therein, a drug-containing formulation containing (a) an agent susceptible to inducing sensitization of the skin or mucosa when the drug is administered transdermally or transmucosally via electrotransport at a therapeutically effective rate, and (b) a countersensitizing agent selected from the group consisting of cis-urocanic acid and analogs thereof, in an amount effective to prevent or inhibit sensitization upon electrotransport administration of the drug, wherein the device is adapted to be placed in drug- and agent-transmitting relation to the skin or mucosa, with at least one of the electrodes associated with the reservoir.

17. The electrotransport drug delivery device of claim 16, wherein the sensitizing agent is the drug, an excipient, an ion exchange resin, or a polymeric matrix component.

18. The electrotransport drug delivery device of claim 16, wherein the sensitizing agent is the drug.

19. The electrotransport drug delivery device of claim 16, wherein the drug is one that is susceptible to inducing sensitization when administered via electrotransport at a therapeutically effective rate.

20. The electrotransport drug delivery device of claim 16, wherein the countersensitizing agent is cis-urocanic acid.

21. The electrotransport drug delivery device of claim 16, wherein the countersensitizing agent is an analog of cis-urocanic acid.

22. The electrotransport drug delivery device of claim 16, wherein the analog of cis-urocanic acid is selected from the group consisting of cis and trans isomers of 2-methylurocanic, cis and trans isomers of 1-furanacrylic acid, cis and trans isomers of 2-pyrrole acrylic acid, cis and trans isomers of 2-thiopheneacrylic acid, cis and trans isomers of 3-thiopheneacrylic acid, dihydrourocanic acid, imidazolepyruvic acid, imidazoleacetic acid, hydantoin 5-propionic acid, 2-pyridineacrylic acid, 3-pyridineacrylic acid, and imidazolonepropionic acid.

23. The electrotransport drug delivery device of claim 16, wherein the analog of cis-urocanic acid is 2-methylurocanic acid.

24. The electrotransport drug delivery device of claim 16, wherein the countersensitizing agent is administered at a rate effective to inhibit the induction of sensitization.

25. The electrotransport drug delivery device of claim 16, wherein the formulation has a pH at which both the drug and the countersensitizing agent are anionic.

26. The electrotransport drug delivery device of claim 16, wherein that formulation has a pH at which both the drug and the countersensitizing agent are cationic.

27. The electrotransport drug delivery device of claim 16, wherein the formulation has a pH at which the drug is cationic and at least a portion of the cis-urocanic acid has a neutral charge.

28. The electrotransport drug delivery device of claim 16, wherein the formulation has a pH at which one of the drug and countersensitizing agent is cationic and the other is anionic and further wherein both are administered from the reservoir by an alternating polarity electrotransport current.

* * * * *

UNITED STATES PATENT AND TRADEMARK OFFICE
CERTIFICATE OF CORRECTION

PATENT NO. : 5,995,869
DATED : Nov. 30, 1999
INVENTOR(S) : Cormier et al.

It is certified that error appears in the above-identified patent and that said Letters Patent is hereby corrected as shown below:

In Claim 4, column 13, line 68, "redetermined" should read, --predetermined--.

In Claim 6, column 14, line 5, "ti" should read --to--.

Signed and Sealed this

Eighth Day of August, 2000

Attest:

Q. TODD DICKINSON

Attesting Officer

Director of Patents and Trademarks